United States Patent
Weidner et al.

(10) Patent No.: US 10,556,128 B2
(45) Date of Patent: Feb. 11, 2020

(54) APPARATUS FOR AN X-RAY DEVICE

(71) Applicant: SIEMENS HEALTHCARE GMBH, Erlangen (DE)

(72) Inventors: Tom Weidner, Erlangen (DE); Ulf Zimmermann, Aurachtal (DE); Stefan Veitenhansl, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/055,350

(22) Filed: Aug. 6, 2018

(65) Prior Publication Data
US 2019/0038917 A1   Feb. 7, 2019

(30) Foreign Application Priority Data
Aug. 4, 2017   (DE) .................. 10 2017 213 610

(51) Int. Cl.
*A61B 6/08*   (2006.01)
*A61N 5/10*   (2006.01)
*A61B 6/00*   (2006.01)

(52) U.S. Cl.
CPC ............. *A61N 5/1048* (2013.01); *A61B 6/08* (2013.01); *A61B 6/4035* (2013.01); *A61N 2005/1095* (2013.01)

(58) Field of Classification Search
CPC ... A61B 6/06; A61B 6/08; G21K 1/02; G21K 1/04
See application file for complete search history.

(56) References Cited

U.S. PATENT DOCUMENTS

| | | | |
|---|---|---|---|
| 2,405,444 A | 8/1946 | Moreau et al. | |
| 3,717,768 A | 2/1973 | Edholm et al. | |
| 9,049,996 B2 * | 6/2015 | Tsujii | A61B 6/022 |
| 2012/0087478 A1 | 4/2012 | Brown et al. | |
| 2013/0322594 A1 * | 12/2013 | Tsujii | A61B 6/022 378/41 |
| 2014/0254754 A1 * | 9/2014 | Ikarashi | G01N 23/04 378/62 |
| 2019/0038917 A1 * | 2/2019 | Weidner | A61B 6/08 |

FOREIGN PATENT DOCUMENTS

| | | |
|---|---|---|
| DE | 2105259 A1 | 8/1971 |
| FR | 2514519 A | 4/1983 |

* cited by examiner

*Primary Examiner* — Thomas R Artman
(74) *Attorney, Agent, or Firm* — Laurence Greenberg; Werner Stemer; Ralph Locher

(57) ABSTRACT

With a screen-filter-mirror unit installed in a sandwich architecture, an x-ray window on a patient or an object can also be visualized during an x-ray recording with a light window. It is advantageous that a screen, a filter and a light window unit are combined in just one unit and with a changing x-ray window only the unit is replaced and/or the attack angle of the unit and the alignment of a light source directed hereto can be attuned to one another.

8 Claims, 5 Drawing Sheets

APPARATUS FOR AN X-RAY DEVICE

CROSS-REFERENCE TO RELATED APPLICATION

This application claims the priority, under 35 U.S.C. § 119, of German application DE 10 2017 213 610.3, filed Aug. 4, 2017; the prior application is herewith incorporated by reference in its entirety.

BACKGROUND OF THE INVENTION

Field of the Invention

X-ray devices have at least one filter unit for changing the x-ray beam quality and a screen unit for localizing an x-ray window or x-ray field of an x-ray source. The filter unit can have a plurality of different filters in an alternate arrangement, for instance a filter wheel, and can position at least one filter in each case upstream of an x-ray recording in the x-ray beam path. The screen unit can have a plurality of controllable screens, which, after defining the x-ray window, are moved into its x-ray beam path prior to releasing the x-rays of the x-ray source. In addition, a unit for visualizing the x-ray window can be arranged on the patient at the output of an x-ray source, for instance. This unit is referred to below as light window unit. Components of this light window unit are a light source and a mirror which projects the light beams originating from this light source onto the object area to be irradiated which is equivalent to the x-ray field or x-ray window. The cited units are combined in a collimator and arranged downstream of the x-ray source. The light window unit for visualizing the x-ray field is integrated here as a first unit and the filter and screen unit are integrated downstream in the collimator. In a compact design of the collimator with filter, screen and a light window unit, the selection and positioning of the filter and the visualization of the x-ray window are carried out separately in terms of time. In the light window unit, prior to an x-ray recording, a mirror for deflecting the light beams output by a light source is moved out of a standby position and back into this prior to releasing the x-ray radiation for an x-ray recording. The light output by the light source is deflected by way of the mirror and localized by the positioned screens of the screen unit. The light window projected onto the surface of the patient corresponds to the x-ray field or x-ray window. After removing the mirror from the x-ray beam path, a filter selected for a requisite x-ray quality is then introduced herein for the x-ray recording. This is disadvantageous in that prior to an x-ray recording the x-ray window is only visualized to the physician or assistant through the light window. An alignment of screen elements of the screen unit can be carried out manually and/or semi-manually or electronically. Aside from the disadvantage of its complex or narrow structure, the embodiment of the collimator is further disadvantageous in that the motorized screen elements of the screen unit may result in a restriction to the selective fade-in options in the boundary areas of the x-ray window when positioning the same. With x-ray devices with a very hard radiation spectrum, such as, for instance >>50 kV, conventional mirrors applied on a glass carrier basis are used for instance, and remain in the beam path during the x-ray recording. With x-ray devices which are used for mammography recordings and/or tomosynthesis recordings, the presence of a mirror of this type in the x-ray beam path on account of beam hardening results in a higher absorption of the x-ray radiation and as a result in a worsening of the mammography or tomosynthesis image.

SUMMARY OF THE INVENTION

The object underlying the invention is to disclose an apparatus in which the cited disadvantages are overcome.

The subject matter of the invention has a screen-filter-mirror unit, with which a localization of the x-ray window with a base plate having at least one cutout is provided. The cutout has a filter unit, wherein its surface is additionally embodied such that light can be reflected herefrom.

The collimator to be arranged between the x-ray source and detector has a screen-filter-mirror unit, wherein the screen-filter-mirror unit arranged in a collimator can be aligned and a light window corresponding to an x-ray window can be mapped onto an object or a patient.

The subject matter of the invention is advantageous in that a fading-in, a filtering of the x-rays and a reflective layer for generating a light window are combined in a compact apparatus.

The invention is advantageous in that the screen, filter and light window unit are combined in just one unit and with a changing x-ray window only the unit is replaced and/or the attack angle of the unit and the alignment of a light source directed hereto can be attuned to one another.

The invention is advantageous in that even during an x-ray recording with a filter a reflective layer for a light window remains in the x-ray beam path for a mammography recording.

The invention is advantageous in that aside from a compact, space-saving apparatus, an x-ray window can also be positioned in the boundary areas of the detector and a visualization of the x-ray window on a patient also takes place during an x-ray recording, without the x-ray spectrum being influenced.

The invention is advantageous in that an x-ray filter with a corresponding x-ray window can be selected in a patient-specific manner by replacing an insertion element and a light window or light field which corresponds to the x-ray window can be mapped on a patient.

The invention is advantageous in that in a compact manner in a sandwich architecture this also visualizes an x-ray window on a patient or an object during an x-ray recording with a light window.

The invention is advantageous in that at least one fin arranged in the collimator can be aligned and/or activated such that the x-ray window formed by a cutout in the base plate is partially minimized or can be faded out or concealed on the patient or object.

The invention is advantageous in that the light beams of a light source can be deflected according to the propagation of the x-ray beam of the x-ray source using at least one light-reflecting layer and/or light-reflecting surface of the alignable screen-filter-mirror unit.

The invention is advantageous in that the screen-filter-mirror unit can be positioned and aligned in a collimator such that the light source directed at a light-reflecting layer and/or light-reflecting surface of the screen-filter-mirror unit deflects the light beams originating herefrom on the light-reflecting layer and/or light-reflecting surface in the direction of the object and on an object positioned on the object couch maps a light window which corresponds to the x-ray window on the object.

Other features which are considered as characteristic for the invention are set forth in the appended claims.

Although the invention is illustrated and described herein as embodied in an apparatus for an x-ray device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

With an alignable screen-filter-mirror unit which is formed in the sandwich architecture and a light source which can likewise be aligned with this unit, an x-ray window positioned on an object in accordance with the dimensions of an x-ray beam and having a light window can also be positioned and visualized during an x-ray recording.

Figure 1:
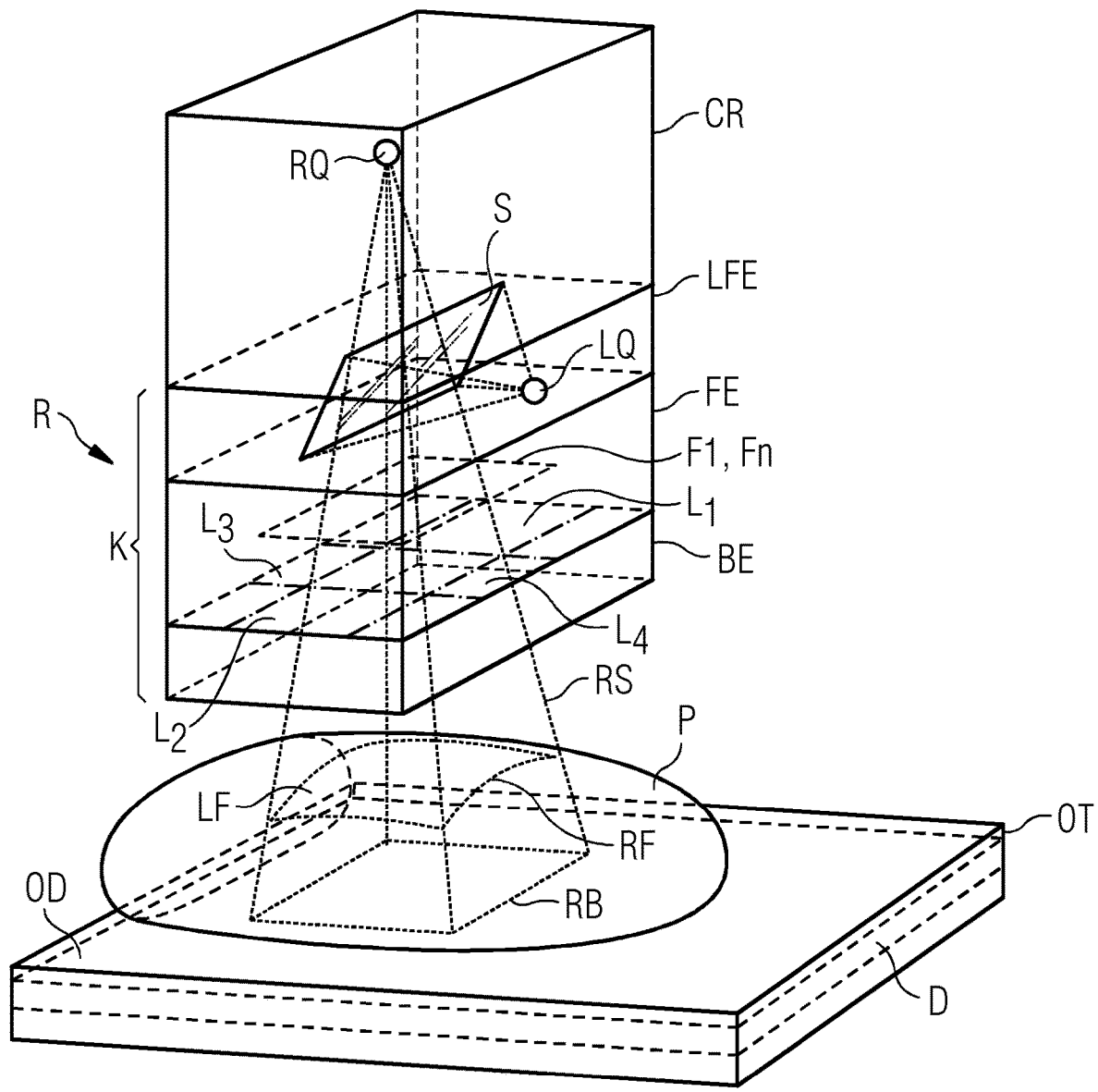
FIG. 1 is a diagrammatic, perspective view of an x-ray detector unit with a collimator according to the invention.

Referring now to the figures of the drawings in detail and first, particularly to FIG. 1 thereof, there is shown a schematic representation of an X-ray system R with an x-ray source RQ, a collimator K arranged downstream of an x-ray source RQ and a detector D for recording the x-ray beams RS routed through a patient or an object P from the x-ray source RQ. The detector D and possibly a grid above the detector D are arranged within a vertically movable and rotatable object couch OT. A breast can be positioned on the surface OD of the object couch OT and compressed by a compression plate which can be moved in terms of height and is not shown explicitly in this drawing. In this embodiment variant, the collimator K containing a number of units LFE, FE, BE is arranged downstream of a chassis CR of the x-ray source RQ. At least one light window unit LFE, a filter unit FE and a screen unit BE are integrated in the collimator K. Electronically controllable fins L1, L2, L3 and L4 can be positioned in the screen unit BE such that the x-rays RS originating from the x-ray source RQ are limited to a region to be examined on the patient or object P. A corresponding x-ray image RB can then be read out from a detector D. In the filter unit FE disposed thereabove, at least one first filter unit F1 is moved into the x-ray beams RS originating from the x-ray source RQ. The selection and positioning of a filter Fx can take place manually or for instance from a filter F1, ..., Fn deposited in a rotatable filter plate. The selection from this supply inventory can be implemented electronically by activating the rotatable filter plate. A manual incorporation of a filter Fn in guide rails provided herefor into the rotatable filter plate or directly in the filter unit FE is likewise possible. At least one positionable mirror S with a light source LQ which can be pivoted in and/or out or aligned is arranged in the light window unit LFE which can be arranged upstream of the filter unit FE. In this embodiment variant, the mirror S is removed from the indicated x-ray beam RS again prior to an x-ray recording.

Figure 2:
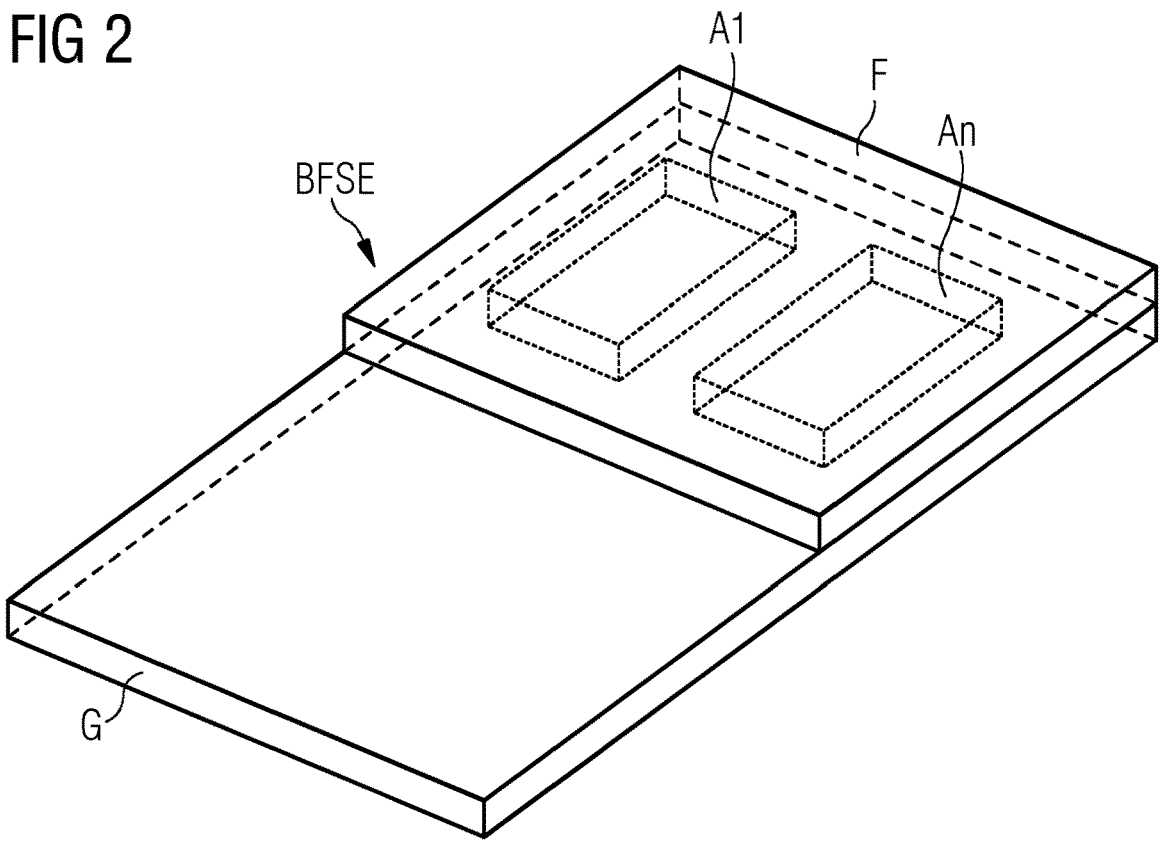
FIG. 2 is a perspective view of an embodiment variant of a screen-filter-mirror unit.

FIG. 2 shows a first exemplary embodiment of a screen-filter-mirror unit BFSE according to the invention. The screen-filter-mirror unit BFSE is realized in a sandwich architecture, for instance. The basis for this sandwich architecture here forms a base plate G which is impermeable to or absorbs x-ray radiation. The base plate G can be made of steel or lead or another highly absorbent material, for instance. The base plate G has one or more cutouts A1, ..., An to allow x-rays RS to pass. The cutouts A1, ..., An can be incorporated into the base plate G at any point. The filters Fn required for the x-ray examination can be positioned in, on, or below these cutouts A1, ..., An on the base plate G. In the embodiment variant shown, a filter F embodied as a film or a very thin plate like for instance made from the filter material Al, Rh or Ti is arranged above the cutouts A1, ..., An. A mirroring facing toward the light source can be vapor deposited onto this film or the very thin plate. In the case of incompatibility between the filter material and the material for the base plate G, a separating layer, for instance a lacquer coat or a plastic film can be applied or arranged therebetween. With the use of the screen-filter-mirror unit BFSE, depending on the application, one or more cutouts A1, ..., An can be incorporated herein. A selective fading-out of the x-ray beam RS as far as one or more cutouts Ax, Ay in the base plate G is possible. To this end one or more cutouts Ax, ..., Ay are covered with motorized screen fins L1, ..., L4 which are arranged in the collimator K. The screen fins L1, ..., L4 are, as shown by way of example in FIG. 1, 5, arranged below the filter unit. The filter F1, Fn formed as a film for instance can be arranged on the side of the base plate G which faces the light source LQ, see FIG. 5. In order to increase the light reflection the surface of the filter Fn which faces the light source LQ can be polished or provided with an extremely thin reflective layer. The screen-filter-mirror unit BFSE can either be positioned in an embodiment of a collimator K, see here FIGS. 5, 6 or in an existing collimator K as shown in FIG. 1 in a rotatable filter plate. The movable mirror, as shown and described in FIG. 1, would then be parked in the interim in a stationary position, outside of the x-ray beams RS. At least parts of the surface can be embodied on the side of the screen-filter-mirror unit BFSE which faces a light source LQ to be integrated within the collimator K such that sufficient light for a light window LF to be mapped onto an object P or a detector surface is reflected. In a further embodiment variant, a light-absorbing layer NLRL can be applied to the underside of the base plate G outside of the cutout/cutouts A1, ..., An. Aside from the cutouts, this light-absorbing layer NLRL can have additional cutouts for the light reflection, see FIG. 6.

Figure 3:
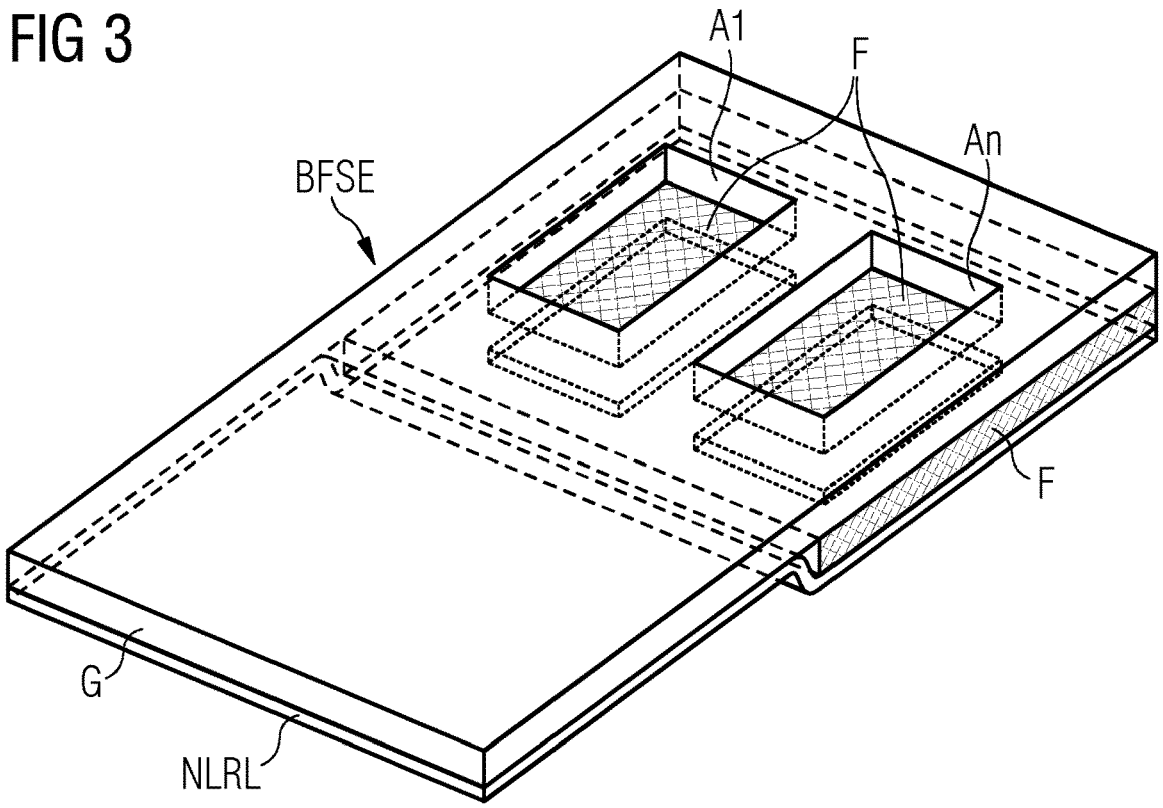
FIG. 3 is a perspective view of a further embodiment variant of a screen-filter-mirror unit.

FIG. 3 shows a further schematic embodiment of a combined screen-filter-mirror unit BFSE. In this embodiment, the filter F is arranged in the form of a film F below the base plate G, for instance. The film F can extend across the entire base plate G or only across individual cutouts A1, ..., An. It is also conceivable for a first filter F1 to be positioned in a first cutout A1 and a further filter Fn to be positioned in a further cutout An. A layer NLRL which does not reflect light is applied to the underside of the film F outside of the cutouts A1, An. The side which faces the light source LQ is polished such that a light-reflecting surface S is formed and the light is reflected herefrom.

Figure 4:
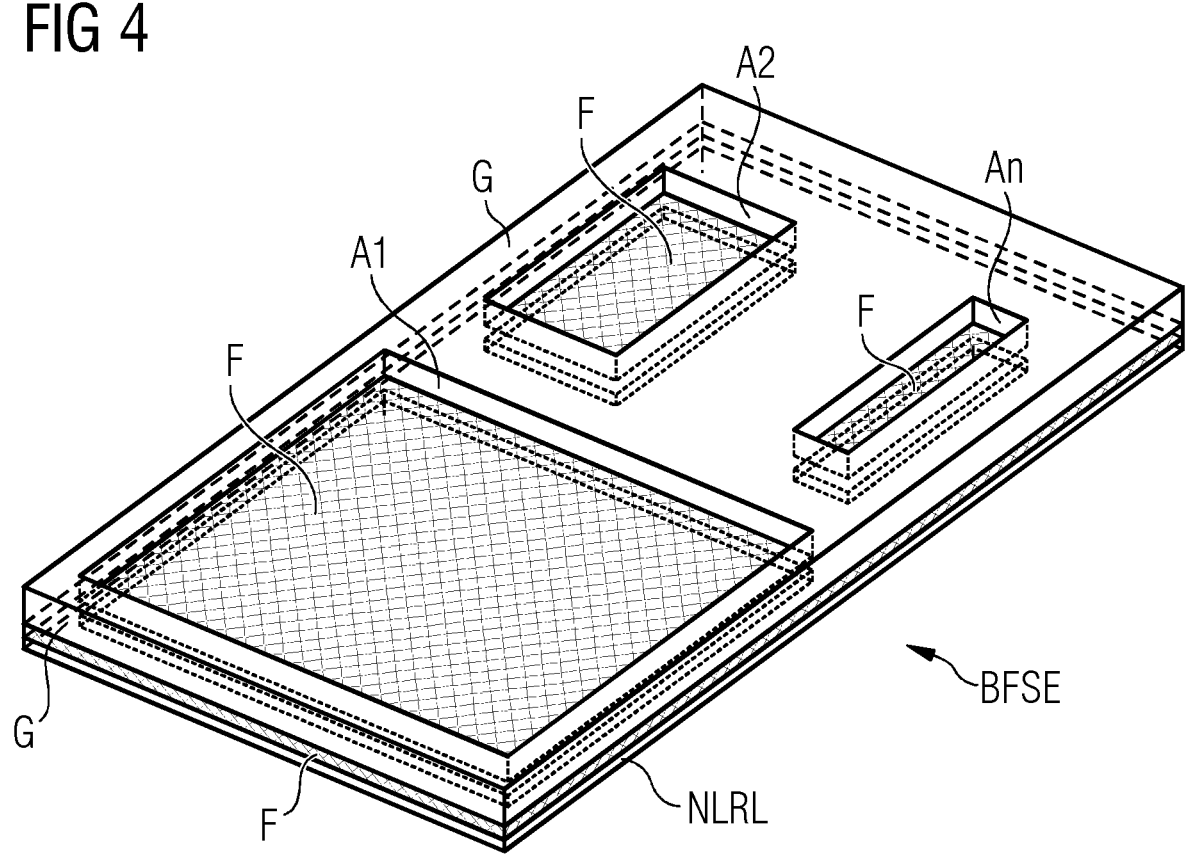
FIG. 4 is a perspective view of a further embodiment variant of a screen-filter-mirror unit.

FIG. 4 shows a further embodiment variant of a screen-filter-mirror unit BFSE. In this embodiment, a larger cutout A1 and/or at least one smaller cutout A2, An can be positioned individually or in combination in the base plate G. This is then advantageous when a region for positioning a biopsy is additionally or separately provided in the boundary area of the object couch OT for instance and is to be marked with a light window. In regions outside of the cutouts A1, . . . , An, a non-reflective coating NLRL can, as indicated in FIG. 4, be applied to the filter F. In order to visualize or optically highlight the x-ray window RF on the patient P or a region on the object couch OT, a light-reflective layer S embodied on the underside of the filter F, which can also be referred to as reflective layer, could be highlighted differently, so that a region for depositing a biopsy on the object couch OT is highlighted or can be marked especially for instance.

Figure 5:
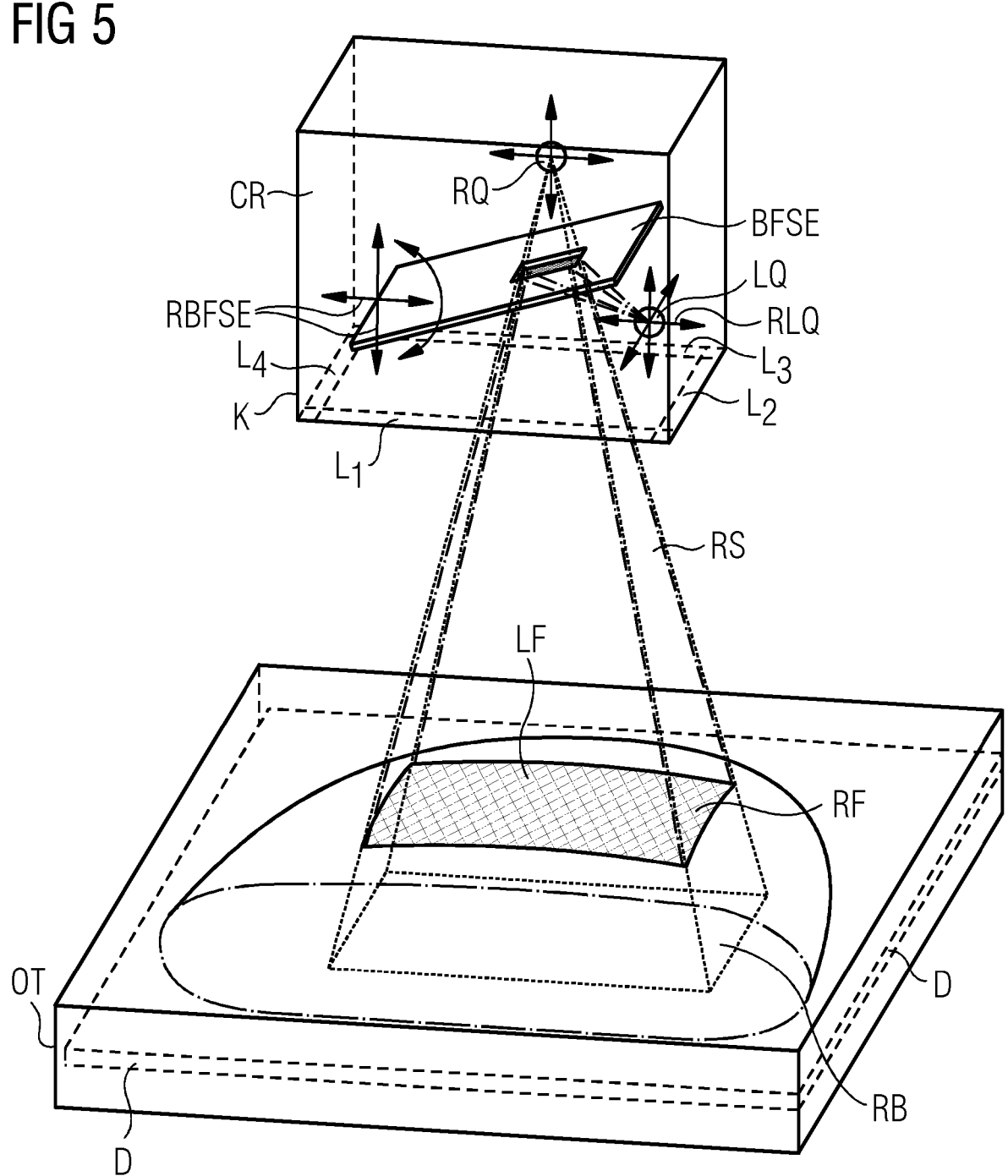
FIG. 5 is a perspective view of an arrangement of an embodiment variant of a screen-filter-mirror unit.

FIG. 5 schematically shows an embodiment of the invention of an x-ray detector arrangement with a collimator K arranged at the output of the x-ray source RQ. A screen-filter-mirror unit BFSE is arranged in the collimator K. The positionable x-ray source RQ and a positionable light source LQ are disposed above and below the positionable screen-filter-mirror unit BFSE in each case. The alignment of the x-ray source RQ, the inclination RBFSE of the screen-filter-mirror unit BFSE and the alignment RLQ of the light source LQ of the filter FN of the screen-filter-mirror unit BFSE beamed from the x-ray source RQ can be fixedly set for a filter window. A screen-filter-mirror unit BFSE with just one positioned cutout or a cover of selected cutouts Ax, Ay is likewise possible. An x-ray window RF can be disposed entirely at the edge and/or in the center of the detector D, for instance. The position and/or inclination of the screen-filter-mirror unit BFSE, the positioning and/or alignment of the x-ray source RQ and the light source LQ can be matched to one another. The tuning can take place manually, semi-manually or automatically or in a processor-controlled manner. The selection of the x-ray window and/or the x-ray window RF and the respective coordination of the alignments of the screen-filter-mirror unit BFSE and the light source LQ which are to be attuned to one another can take place by means of a microprocessor in a control unit, not shown explicitly here. The fins L1, . . . ,L4 indicated in the collimator K can optionally be activated and thus actively conceal a filter Fx on the screen-filter-mirror unit BFSE or are released for x-rays RS of the x-ray source RQ.

Figure 6:
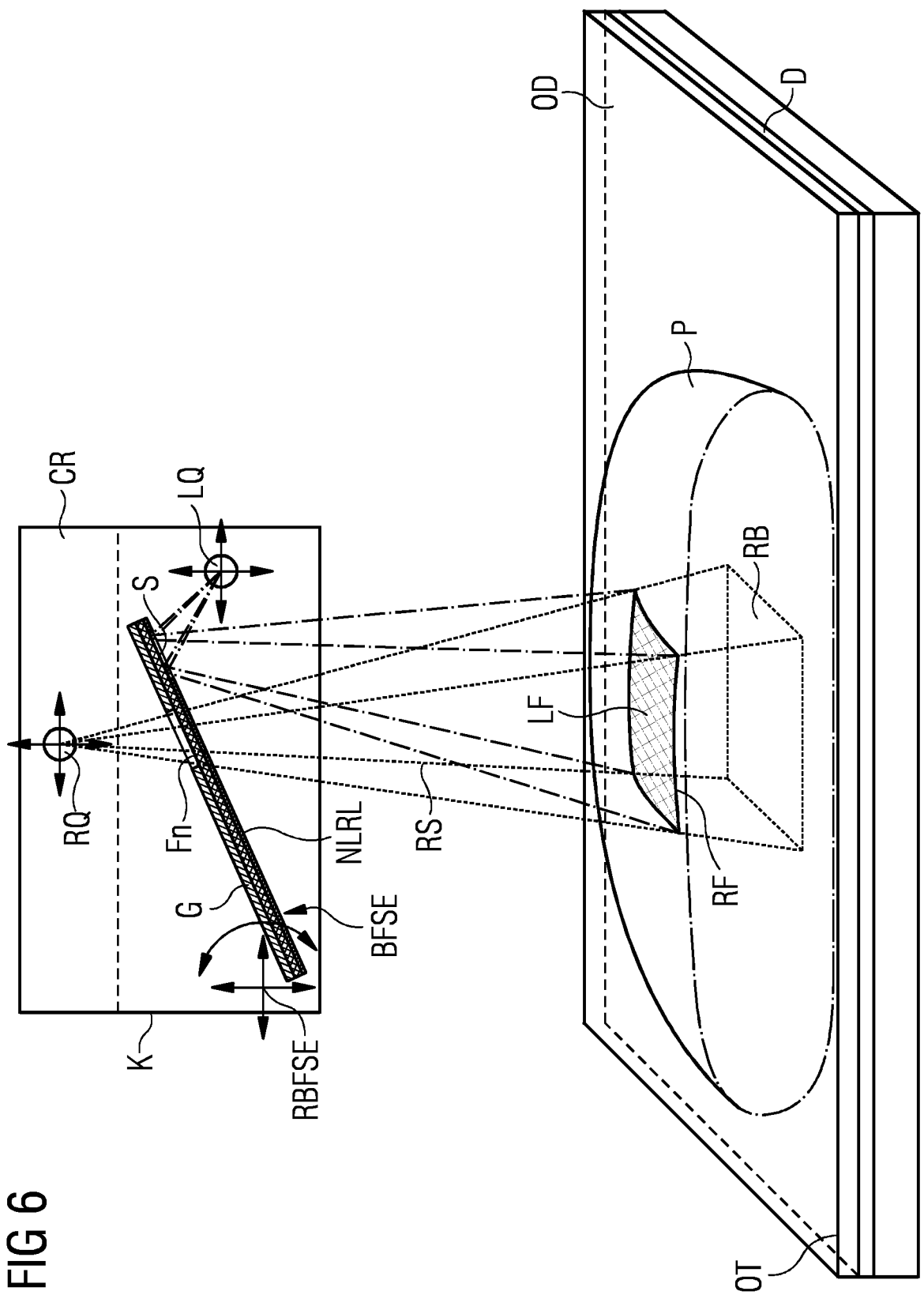
FIG. 6 is a perspective view of a further embodiment of an arrangement with an embodiment variant of a screen-filter-mirror unit.

Similarly to in FIG. 5, an x-ray detector arrangement with a further embodiment of a collimator K is shown schematically in FIG. 6. In this embodiment, a screen-filter-mirror unit BFSE is embodied in the collimator K such that the reflective layer or surface S embodied on the rear of the filter Fn can be arranged separately from the surface of the filter Fn or the site of the cutouts An on the base plate G. In this embodiment the light source LQ can be aligned with the reflective layer or surface S such that the reflected light of the light source LQ marks the x-ray window RF on an object P and/or a region on the surface OD of the object couch OT. The light source LQ is positioned within the collimator K and aligned with a reflective surface such that using a light window LF the irradiated area on a patient P or a specific area on the surface OD of the object couch OT is visualized. The light source LQ can also be positioned and aligned such that depending on the choice of a screen-filter-mirror unit BFSE, a filter Rn forms an x-ray window RF and a corresponding light window LF on the breast of a patient P or on the object couch OT for instance.

The following is a summary list of reference numerals and the corresponding structure used in the above description of the invention:
R x-ray system
RQ x-ray source
L couch
RS x-ray beam
RF x-ray window
RB x-ray image
CT chassis for x-ray source
K collimator
LFE light window unit
LF light window
LQ light source
FE filter unit
S light-reflecting layer, -surface
FE filter unit
F1, Fm first filter, n'th filter
BE screen unit
L1, L2, L3, L4 first, second, third, fourth fin,
P patient/object
OD surface detector
D detector
OT object couch
BFSE screen-filter-mirror unit
A1, . . . An first, . . . , n'th cutout
NLRL non-reflective layer

The invention claimed is:

1. An apparatus, comprising:
a filter unit for homogenizing x-ray beams output by an x-ray source;
an alignable screen-filter-mirror unit for localizing an x-ray window and having a base plate with at least one cutout formed therein, said filter unit disposed in said at least one cutout; and
said filter unit having a filter layer with a light-reflecting layer and/or light-reflecting surface, said light-reflecting layer and/or light-reflecting surface of said filter unit is formed on a side of said base plate facing a light source.

2. The apparatus according to claim 1, wherein said filter unit is embodied in a form of a film or a plate.

3. The apparatus according to claim 1, wherein said filter unit is disposed in and/or on and/or under said at least one cutout of said base plate.

4. The apparatus according to claim 1, wherein said alignable screen-filter-mirror unit is designed in a sandwich architecture.

5. The apparatus according to claim 1, wherein light beams of the light source can be deflected according to a propagation of an x-ray beam of the x-ray source using said at least one light-reflecting layer and/or light-reflecting surface of said filter unit.

6. The apparatus according to claim 1, wherein the light source can be positioned and aligned.

7. The apparatus according to claim 1, further comprising a collimator, said alignable screen-filter-mirror unit can be positioned and aligned in said collimator such that the light source directed at said light-reflecting layer and/or light-reflecting surface of said alignable screen-filter-mirror unit deflects light beams originating herefrom on said light-reflecting layer and/or light-reflecting surface in a direction of an object and on the object positioned on an object couch maps a light window corresponding to the x-ray window on the object.

8. The apparatus according to claim 7, further comprising at least one fin disposed in said collimator and can be aligned and/or activated such that the x-ray window formed by said cutout in said base plate can be partially minimized or faded-out on a patient or the object.

\* \* \* \* \*